United States Patent [19]

Strebelle et al.

[11] Patent Number: 5,254,777
[45] Date of Patent: Oct. 19, 1993

[54] CATALYTIC HYDROCHLORINATION SYSTEM AND PROCESS FOR THE MANUFACTURE OF VINYL CHLORIDE FROM ACETYLENE AND HYDROGEN CHLORIDE IN THE PRESENCE OF THIS CATALYTIC SYSTEM

[75] Inventors: Michel Strebelle, Brussels; André Devos, Sint-Stevens-Woluwe, both of Belgium

[73] Assignee: Solvay (Société Anonyme), Brussels, Belgium

[21] Appl. No.: 901,168

[22] Filed: Jun. 18, 1992

[30] Foreign Application Priority Data

Jun. 20, 1991 [BE] Belgium ............................. 9100600

[51] Int. Cl.⁵ .............................................. C07C 17/08
[52] U.S. Cl. ...................................... 570/233; 502/167
[58] Field of Search ........................................... 570/233

[56] References Cited

U.S. PATENT DOCUMENTS 4,912,271 3/1990 Thelen et al. ....................... 570/233

FOREIGN PATENT DOCUMENTS 090443 5/1983 European Pat. Off. .
237116 6/1979 U.S.S.R. .
2001546 7/1979 United Kingdom .

OTHER PUBLICATIONS

Abstract 00683A, Derwent Publications Ltd., Electro-Chemical IND KK, JA 52/136104 1977.
JA 52/136103, Electro-Chemical IND, JA 52/136103 (English Translation) 1977.
Chemical Abstracts, vol. 71 —12510v 1969.

Primary Examiner—Howard T. Mars
Attorney, Agent, or Firm—Spencer, Frank & Schneider

[57] ABSTRACT

Liquid catalytic system comprising at least one group VIII metal compound, a fatty amine hydrochloride whose melting point is greater than 25° C. and an organic solvent. This catalytic system is suitable for the preparation of vinyl chloride by reacting acetylene with hydrogen chloride.

6 Claims, No Drawings

CATALYTIC HYDROCHLORINATION SYSTEM AND PROCESS FOR THE MANUFACTURE OF VINYL CHLORIDE FROM ACETYLENE AND HYDROGEN CHLORIDE IN THE PRESENCE OF THIS CATALYTIC SYSTEM

The present invention relates to a liquid catalytic hydrochlorination system based on a group VIII metal compound and to a process for the manufacture of vinyl chloride by hydrochlorination of acetylene in the presence of such a catalytic system.

The manufacture of vinyl chloride by reaction between acetylene and hydrogen chloride is commonly carried out in the gas phase, in a fixed bed reactor, in the presence of a heterogeneous solid catalyst based on mercury chloride on a support. Chiefly for reasons of toxicity, there currently exists a growing interest in catalytic systems which are free from mercury compounds. Various catalysts intended to replace the current catalysts in the gas phase processes have been developed. For example, the unexamined Japanese Patent Application 52/136104 describes a process for hydrochlorination of acetylene in the gas phase in the presence of a fixed bed of catalyst consisting of noble metal halides deposited on active charcoal. Until now, however, the lifetimes of such alternative catalysts intended for gas phase processes remain very much shorter than those of catalysts based on mercury compounds.

Moreover, the literature offers certain examples of hydrochlorination of acetylene in the presence of a liquid catalytic medium. German Patent 709,000 describes a process for the preparation of vinyl halides by bringing acetylene into contact, at high temperature, with a molten mass of hydrogen halide salts of organic bases, containing a conventional catalyst. Aliphatic, aromatic or heterocyclic amines and their mixtures are envisaged as organic bases. In Example 1, vinyl chloride is obtained by dispersion of hydrogen chloride and acetylene in a mixture consisting of 350 parts by volume of pyridine, 350 parts by volume of diethylamine and 100 parts by weight of mercury chloride, maintained at 220°–225° C. Author's certificate SU-237,116 describes the use of an acidic aqueous solution containing 46% by weight of cuprous chloride and from 14 to 16% by weight of a methyl-, dimethyl- or trimethylamine hydrochloride. The unexamined Japanese Patent Application 52/136103 discloses a process for the preparation of vinyl chloride by reaction of acetylene with hydrogen chloride in the presence of a catalyst prepared by suspending, in water or in an organic solvent, a binary system selected from gold chloride, platinum chloride and palladium chloride, optionally modified by a chloride of a transition metal of variable valency. Patent Application EP-A-0,340,416 discloses a process for the preparation of vinyl chloride by reaction of acetylene with hydrogen chloride in the presence of a palladium compound as catalyst in a solvent consisting of an aliphatic or cycloaliphatic amide, at a temperature higher than room temperature. Although it allows high yields to be achieved, it would appear that, under the reaction conditions, this catalytic system progressively degrades, forming blackish products of carbonaceous appearance.

Consequently, the objective of the invention is a stable catalytic hydrochlorination system which is free from mercury compounds. Another objective of the invention is to provide a process for the synthesis of vinyl chloride by hydrochlorination of acetylene in the presence of such a liquid catalytic system which is particularly active, which does not degrade under the reaction conditions and which additionally makes it possible to obtain vinyl chloride with a high selectivity and thus to greatly reduce the quantity of by-products to be removed. Unlike the systems based on mercury compounds, the catalytic system according to the invention has the further advantage of avoiding the vaporisation of metal salts in the plant.

The invention relates to a liquid catalytic hydrochlorination system, more particularly for hydrochlorination of acetylene. This catalytic system comprises at least one group VIII metal compound, a fatty amine hydrochloride whose melting point is higher than 25° C. and an organic solvent. Fatty amine means any amine or mixture of amines containing a high number of carbon atoms, for example, more than 8 carbon atoms, which has an unbranched or only slightly branched molecular structure. The preferred amines are those which include from 10 to 20 carbon atoms. This unbranched or only slightly branched molecular structure allows an easy crystallisation of the hydrochloride formed by reaction of the fatty amine with hydrogen chloride and explains the high melting points of the hydrochlorides of these compounds. Amines corresponding to the defintion of fatty amine above are, for example, decylamine, undecylamine, dodecylamine or 3-methyldodecylamine.

Good results were obtained with a catalytic system comprising dodecylamine hydrochloride.

The group VIII metal compounds used in the catalytic systems of the present invention are generally chosen from iron, cobalt, nickel, ruthenium, rhodium, palladium, osmium, iridium or platinum compounds or from their mixtures. The chlorides of these group VIII metals are preferred, but any other compound which can be converted to chloride in the presence of hydrogen chloride during the preparation of the catalytic system can also be used. Preferably, the group VIII metal compound used in the present invention is chosen from platinum compounds and palladium compounds, such as platinum(II) chloride or palladium(II) chloride or a platinochloride or a palladochloride of alkali metals or of alkaline-earth metals for example, $Na_2(PtCl_4)$, $Na_2(PdCl_4)$, $K_2(PtCl_4)$, $K_2(PdCl_4)$, $Li_2(PtCl_4)$, $Li_2(PdCl_4)$, $(NH_4)_2(PtCl_4)_2(PdCl_4)$ -, hexachloroplatinic acid or its salts, for example $Na_{2pl}\ PtCl_6$, $K_2PtCl_6$, $Li_2PtCl_6$, palladium compounds in which the palladium has a high valency, such as $Na_2PdCl_6$, $K_2PdCl_6$, $Li_2PdCl_6$, etc. It is also possible to use complexes of group VIII metals in which the metal is at 0 valency, such as the $Pt(P\phi_3)_2$, $Pd(P\phi_3)_2$, $(P\phi_3)Pt(CO)$ complexes, etc. Mixtures of group VIII metal compounds can also be used.

The group VIII metal compounds which are particularly preferred are platinum(II) chloride and palladium(II) chloride. The most particularly preferred group VIII metal compound is palladium(II) chloride.

The choice of the nature of the organic solvent used in the process according to the invention is conditioned especially by the necessity that it should be inert with respect to the reactants under the reaction conditions, that it should be miscible with the fatty amine hydrochloride at the reaction temperature and that it should be capable of solubilising the latter at a temperature below its melting point. Moreover, for reasons of safety and of ease of use, preference is given to organic solvents which are not very volatile. The choice of the organic solvent is also influenced by its ability to absorb acetylene. Solvents which satisfy the various criteria set out above are chosen from aliphatic, cycloaliphatic and aromatic hydrocarbons and their mixtures, for example $C_7$ to $C_{15}$ paraffins and alkylbenzenes, especially xylenes, propylbenzenes, butylbenzenes or methylethylbenzenes. For reasons of an economic nature the solvent used is preferably chosen from commercial products consisting of mixtures of aliphatic hydrocarbons such as the Esso solvent Isopar or the Shell solvent Shellsol K or of mixtures of aromatic compounds such as the Esso solvent Solvesso or the Shell solvent Shellsol AB.

Solvents which have given good results are saturated aliphatic solvents, such as the solvent Shellsol K consisting of petroleum cuts which have a boiling point of between approximately 190° C. and approximately 250° C.

Other solvents which may be envisaged on the basis of the various criteria given above are certain heavy halogenated compounds such as haloalkanes, halobenzenes and other halogenated derivatives of aromatic compounds.

The most particularly preferred catalytic system contains dodecylamine hydrochloride, palladium(II) chloride and an aliphatic solvent such as the solvent Shellsol K. Such a catalytic system possesses a high catalytic activity and a selectivity to vinyl chloride which may exceed 99%. Further, this system shows hardly any degradation with time.

The weight ratio of the organic solvent to the fatty amine hydrochloride is generally greater than approximately 0.1. Preferably, this ratio is greater than or equal to approximately 0.5. Under the particularly preferred conditions, it is greater than or equal to approximately 0.8. Generally, this ratio is less than or equal to approximately 20. Preferably, it is less than or equal to approximately 10. Under the particularly preferred conditions, it is less than or equal to approximately 8.

The content of group VIII metal compound in the catalytic system, expressed in millimoles per liter of solution of the catalytic system is generally greater than or equal to approximately 1 mmol/l, preferably greater than or equal to approximately 10 mmol/l. The content of group VIII metal compound in the catalytic system is generally less than or equal to approximately 200 mmol/l, preferably less than or equal to approximately 100 mmol/l. Although it is not indispensable, it is nevertheless preferable that all the group VIII metal compound included in the catalytic system be in the dissolved form.

Generally, the catalytic system is prepared by dissolving or dispersing the required quantity of group VIII metal compound in the fatty amine or in the fatty amine/organic solvent mixture, by heating this solution to a temperature higher than the melting temperature of the fatty amine hydrochloride, and then saturating this solution with hydrogen chloride, resulting in the formation of the fatty amine hydrochloride. It is however also possible, although less easy in practice, to first saturate the fatty amine or the fatty anine/organic solvent mixture, heated beforehand, with hydrogen chloride in order to form the fatty amine hydrochloride and then to introduce the group VIII metal compound into the fatty amine hydrochloride or into the mixture of the latter with the organic solvent afterwards. Usually, the quantity of group VIII metal compound used is such that, in the catalytic system, all the group VIII metal compound is in the dissolved form. It is also possible, however, to use a group VIII metal compound in a quantity or of a nature such that a fraction at least of this compound is present in the catalytic system in a dispersed solid form, without prejudicing the invention.

The invention also relates to a process for the manufacture of vinyl chloride by hydrochlorination of acetylene in the presence of a catalytic system comprising at least one group VIII metal compound, a fatty amine hydrochloride whose melting point is greater than 25° C. and an organic solvent. The nature and the proportions of the constituents of the catalytic system used in the process according to the invention are those defined above.

The process according to the invention can be carried out from room temperature to approximately 200° C. At a higher temperature, the catalytic system has a tendency to rapidly degrade. Generally, the reaction temperature is such that all the fatty amine hydrochloride is in solution. The preferred reaction temperature, that is to say one which offers the best compromise between productivity, yield and stability of the catalytic medium is higher than or equal to approximately 80° C. The best results are obtained at temperatures higher than or equal to approximately 120° C. Preferably, the reaction temperature does not exceed approximately 180° C. A reaction temperature of less than or equal to approximately 170° C. is particularly preferred. The process according to the invention is generally carried out at atmospheric pressure or at a slightly greater pressure compatible with the safety regulations for the handling of acetylene, that is to say not exceeding approximately 1.5 bar.

The process for the manufacture of vinyl chloride by hydrochlorination of acetylene according to the invention is carried out by bringing the gaseous reagents —acetylene and hydrogen chloride—into contact with the liquid catalytic system in any appropriate reactor. The process according to the invention can be carried out conventionally in any apparatus which promotes gas-liquid exchange, such as a plate column or a flooded column containing packing. Another method of use of the process which makes possible good exchange of material between the liquid and gaseous phases consists in using a counterflow reactor, optionally of the sprayed packing bed type, the liquid catalytic system trickling over the stacks, countercurrentwise to the gaseous flow of the reactants.

In the process according to the invention, the molar ratio of the hydrogen chloride to the acetylene introduced into the reactor is generally greater than or equal to approximately 0.5. Preferably, this ratio is greater than or equal to approximately 0.8. Generally, this molar ratio is less than or equal to approximately 3. Good results have been obtained with a molar ratio of the hydrogen chloride to the acetylene introduced into the reactor of less than or equal to approximately 1.5. The acetylene and the hydrogen chloride can be brought into contact inside the reactor or, preferably, mixed prior to their introduction into the reactor.

With the aim of increasing the quantity of acetylene dissolved in the liquid catalytic phase, it is also possible to use a process in which only the acetylene is introduced into the reactor in gaseous form, where it reacts with the hydrogen chloride present in the liquid phase in the hydrochloride form, the fatty amine hydrochloride of the catalytic system being regenerated by bringing a liquid shuttle containing the fatty amine into contact with hydrogen chloride outside the reactor.

The invention is illustrated by the following examples. Examples 1 to 5 are carried out according to the invention. Examples 6(C) to 8(C) are carried out by way of comparison.

EXAMPLES 1 TO 3

The catalytic system is prepared from dodecylamine, from palladium(II) chloride and from the solvent Shellsol K.

The solvent Shellsol K is a commercial product from Shell and consists of a mixture of hydrocarbons, essentially of an aliphatic nature. The product used in these examples has an initial boiling point of 193° C. and a final boiling point of 245° C.

The dodecylamine is first mixed with variable quantities of solvent Shellsol K and then 4 g of palladium(II) chloride, i.e. 22.6 mmol, are introduced with stirring into a liter of solution. The catalytic system is then prepared by saturating the solution with gaseous hydrogen chloride.

The reaction between acetylene and hydrogen chloride is carried out in the following manner:

A Pyrex reactor with an internal volume of 45 ml, equipped with a jacket in which a heat-transfer oil circulates and with a device for introducing the reagents which consists of a nozzle of sintered glass intended to ensure the dispersion of the gases in the liquid medium, is charged with 30 ml of a solution consisting of the dodecylamine, palladium(II) chloride and the solvent Shellsol K.

The solution is heated to 150° C. and a gaseous flow containing a mixture of hydrogen chloride and acetylene in a molar ratio $HCl/C_2H_2$ of 1.17 is introduced into the reactor. The residence time of the gases in the reactor, that is to say the ratio of the volume of the reactor to the volume flow rate of the reagents at the reaction temperature, is 4.9 s. The gaseous product leaving the reactor is analysed by gas phase chromatography. The only reaction products observed are vinyl chloride (VC) and 1-chloroprene (1CPr). The results are collated in Table I. The yield is defined as the molar ratio between the VC produced and the acetylene introduced into the reactor. The selectivity is calculated as the molar ratio of the VC produced to the sum [VC + (2 × 1CPr)].

TABLE I

| Ex. No. | Weight ratio dodecylamine Shellsol K solvent | Yield (%) | VC Produced ($g \cdot h^{-1} \cdot l^{-1}$) | Selectivity (%) | Remarks |
|---|---|---|---|---|---|
| 1 | 50/50 | 42.4 | 258 | 99.2 | |
| 2 | 25/75 | 59.4 | 361 | 97.2 | |
| 3 | 10/90 | 57.3 | 348 | 96.0 | slight degradation of the reaction mixture |

EXAMPLES 4 TO 5

Two catalytic systems are prepared in the same manner as in Example 1 with variable quantities of dodecylamine and of Shellsol K solvent, but the palladium chloride is replaced by 15 mmol/l of platinum (II) chloride.

The hydrochlorination reaction of acetylene is carried out under the same conditions as in Examples 1 to 3. The results are collated in Table II.

TABLE II

| Ex. No. | Weight ratio dodecylamine Shellsol K solvent | Yield (%) | VC Produced ($g \cdot h^{-1} \cdot l^{-1}$) | Selectivity (%) |
|---|---|---|---|---|
| 4 | 25/75 | 5.1 | 31 | 98.9 |
| 5 | 10/90 | 7.6 | 46.2 | 97.0 |

EXAMPLE 6(C)

A catalytic system is prepared in the same manner as in Example 1, but in the absence of organic solvent in the solution. The catalytic system obtained by saturation of the solution is solid, even at 150° C., which makes it impossible to carry out the hydrochlorination reaction of the acetylene in the reactor being used.

EXAMPLE 7(C)

A catalytic system is prepared in the same manner as in Example 1, but in the absence of dodecylamine in solution.

The hydrochlorination reaction of the acetylene is carried out under the same conditions as in the preceding examples. The results are collated in Table III.

EXAMPLE 8(C)

A catalytic system is prepared in the same manner as in Example 1, but the dodecylamine is replaced by dimethylformamide.

The hydrochlorination reaction of the acetylene is carried out under the same conditions as in the preceding examples. The results are collated in Table III.

TABLE III

| Test No. | Yield (%) | VC produced ($g \cdot h^{-1} \cdot l^{-1}$) | Selectivity (%) | Remarks |
|---|---|---|---|---|
| 7(C) | 0.3 | 2 | n.d. | Degradation of the reaction mixture |
| 8(C) | 19 | 116 | 93.4 | Degradation of the reaction mixture |

We claim:

1. A process for the manufacture of vinyl chloride, comprising reacting acetylene with hydrogen chloride in the presence of a liquid catalytic system comprising at least one group VIII metal compound, a fatty amine hydrochloride whose melting point is greater than 25° C. and an organic solvent chosen from the aliphatic, cycloaliphatic and aromatic hydrocarbons and their mixtures to produce vinyl chloride.

2. The process according to claim 1, wherein the fatty amine hydrochloride contains from 10 to 20 carbon atoms.

3. The process according to claim 1, wherein the group VIII metal compound is chosen from compounds of palladium, platinum, and mixtures thereof.

4. The process according to claim 1, wherein the volume ratio between the solvent and the fatty amine hydrochloride varies from approximately 0.1 to approximately 20 and in that the content of group VIII metal compound expressed in millimoles per liter of catalytic system is greater than or equal to approximately 1 mmol/l and less than or equal to approximately 200 mmol/l.

5. The process according to claim 1, wherein the reaction is carried out at a temperature from approximately 80° C. to approximately 180° C.

6. The process according to claim 1, wherein the hydrogen chloride and the acetylene are used in a molar ratio of approximately 0.5 to approximately 3.

* * * * *